U S011209637B2

United States Patent
Matsubara

(10) Patent No.: US 11,209,637 B2
(45) Date of Patent: Dec. 28, 2021

(54) OBSERVATION DEVICE, OBSERVATION CONTROL METHOD, AND OBSERVATION CONTROL PROGRAM THAT CONTROL ACCELERATION OF A MOVEABLE STAGE HAVING AN INSTALLED SUBJECT VESSEL

(71) Applicant: FUJIFILM Corporation, Tokyo (JP)

(72) Inventor: Kenta Matsubara, Ashigarakami-gun (JP)

(73) Assignee: FUJIFILM Corporation, Tokyo (JP)

( * ) Notice: Subject to any disclaimer, the term of this patent is extended or adjusted under 35 U.S.C. 154(b) by 235 days.

(21) Appl. No.: 16/563,094

(22) Filed: Sep. 6, 2019

(65) Prior Publication Data
US 2019/0391376 A1 Dec. 26, 2019

Related U.S. Application Data

(63) Continuation of application No. PCT/JP2018/005098, filed on Feb. 14, 2018.

(30) Foreign Application Priority Data

Mar. 30, 2017 (JP) .............................. JP2017-066765

(51) Int. Cl.
*G02B 21/06* (2006.01)
*G02B 21/12* (2006.01)
*G02B 21/00* (2006.01)

(52) U.S. Cl.
CPC .......... *G02B 21/12* (2013.01); *G02B 21/008* (2013.01); *G02B 21/0032* (2013.01); *G02B 21/0036* (2013.01); *G02B 21/0076* (2013.01)

(58) Field of Classification Search
CPC ................ G02B 21/12; G02B 21/0032; G02B 21/0036; G02B 21/0076; G02B 21/008;
(Continued)

(56) References Cited

U.S. PATENT DOCUMENTS

2005/0058372 A1   3/2005   Engelmann et al.
2008/0165416 A1   7/2008   Ariga et al.
(Continued)

FOREIGN PATENT DOCUMENTS

EP   1757969 A1   2/2007
EP   2209054 A2   7/2010
(Continued)

OTHER PUBLICATIONS

European Office Action for European Application No. 18776072.3, dated May 10, 2021.
(Continued)

*Primary Examiner* — Arnel C Lavarias
(74) *Attorney, Agent, or Firm* — Birch, Stewart, Kolasch & Birch, LLP

(57) ABSTRACT

An observation device includes: a stage on which a vessel in which a subject is stored is installed; an image-forming optical system that includes an objective lens forming an image of the subject stored in the vessel; a scan control unit that moves the stage with respect to the image-forming optical system to scan each observation position in the vessel by the image-forming optical system; and an acceleration-determination-information acquisition unit that acquires at least one piece of information among information about the subject, information about the vessel, information about an observation method, or information about an observation condition. The scan control unit controls an acceleration of the stage on the basis of the at least one piece of information.

17 Claims, 4 Drawing Sheets

(58) Field of Classification Search
CPC .. G02B 21/00; G02B 21/0004; G02B 21/002; G02B 21/0024; G02B 21/06; G02B 21/08; G02B 21/082; G02B 21/084; G02B 21/086; G02B 21/088; G02B 21/14; G02B 21/26; G02B 21/34; G02B 21/36; G02B 21/361; G02B 21/365
USPC ....... 359/385, 362, 363, 368, 369, 388, 389, 359/390, 391, 392, 393, 396, 398
See application file for complete search history.

(56) References Cited

U.S. PATENT DOCUMENTS

| | | | |
|---|---|---|---|
| 2009/0148153 A1* | 6/2009 | Minamide | G02B 21/365 396/432 |
| 2009/0311734 A1 | 12/2009 | Greve et al. | |
| 2010/0047902 A1 | 2/2010 | Uozumi et al. | |
| 2010/0179698 A1 | 7/2010 | Oda et al. | |
| 2011/0115897 A1* | 5/2011 | Najmabadi | G01N 21/64 348/79 |
| 2012/0026582 A1 | 2/2012 | Okabe et al. | |

FOREIGN PATENT DOCUMENTS

| | | |
|---|---|---|
| JP | 2005-31664 A | 2/2005 |
| JP | 2008-170641 A | 7/2008 |
| JP | 2009-537021 A | 10/2009 |
| JP | 2010-161950 A | 7/2010 |
| JP | 2012-27387 A | 2/2012 |
| JP | 2016-212337 A | 12/2016 |
| WO | WO 2007/001002 A1 | 1/2007 |

OTHER PUBLICATIONS

International Preliminary Report on Patentability and Written Opinion of the International Searching Authority, dated Oct. 10, 2019, for International Application No. PCT/JP2018/005098, with an English Translation.
International Search Report, dated May 15, 2018, for International Application No. PCT/JP2018/005098, with an English translation.
Japanese Office Action for Japanese Application No. 2019-508726, dated Apr. 14, 2020, with English translation.
Korean Office Action for corresponding Korean Application No. 10-2019-7025377, dated Sep. 23, 2020, with English translation.
Extended European Search Report, dated Feb. 26, 2020, for European Application No. 18776072.3.
Japanese Office Action, dated Jul. 21, 2020, for Japanese Application No. 2019-508726, with an English machine translation.

* cited by examiner

FIG. 4A

PHASE-DIFFERENCE OBSERVATION METHOD

|  |  | TYPE OF CULTURE MEDIUM | | |
|---|---|---|---|---|
|  |  | B1 | B2 | B3 |
| TYPE OF CULTURE VESSEL | 6 WELLS | A1 | A2 | A3 |
|  | 12 WELLS | A4 | A5 | A6 |
|  | 48 WELLS | A7 | A8 | A9 |
|  | 96 WELLS | A10 | A11 | A12 |

FIG. 4B

BRIGHT-FIELD OBSERVATION METHOD

|  |  | TYPE OF CULTURE MEDIUM | | |
|---|---|---|---|---|
|  |  | B1 | B2 | B3 |
| TYPE OF CULTURE VESSEL | 6 WELLS | A13 | A14 | A15 |
|  | 12 WELLS | A16 | A17 | A18 |
|  | 48 WELLS | A19 | A20 | A21 |
|  | 96 WELLS | A22 | A23 | A24 |

FIG. 4C

EPIFLUORESCENCE OBSERVATION METHOD

|  |  | TYPE OF CULTURE MEDIUM | | |
|---|---|---|---|---|
|  |  | B1 | B2 | B3 |
| TYPE OF CULTURE VESSEL | 6 WELLS | A25 | A26 | A27 |
|  | 12 WELLS | A28 | A29 | A30 |
|  | 48 WELLS | A31 | A32 | A33 |
|  | 96 WELLS | A34 | A35 | A36 |

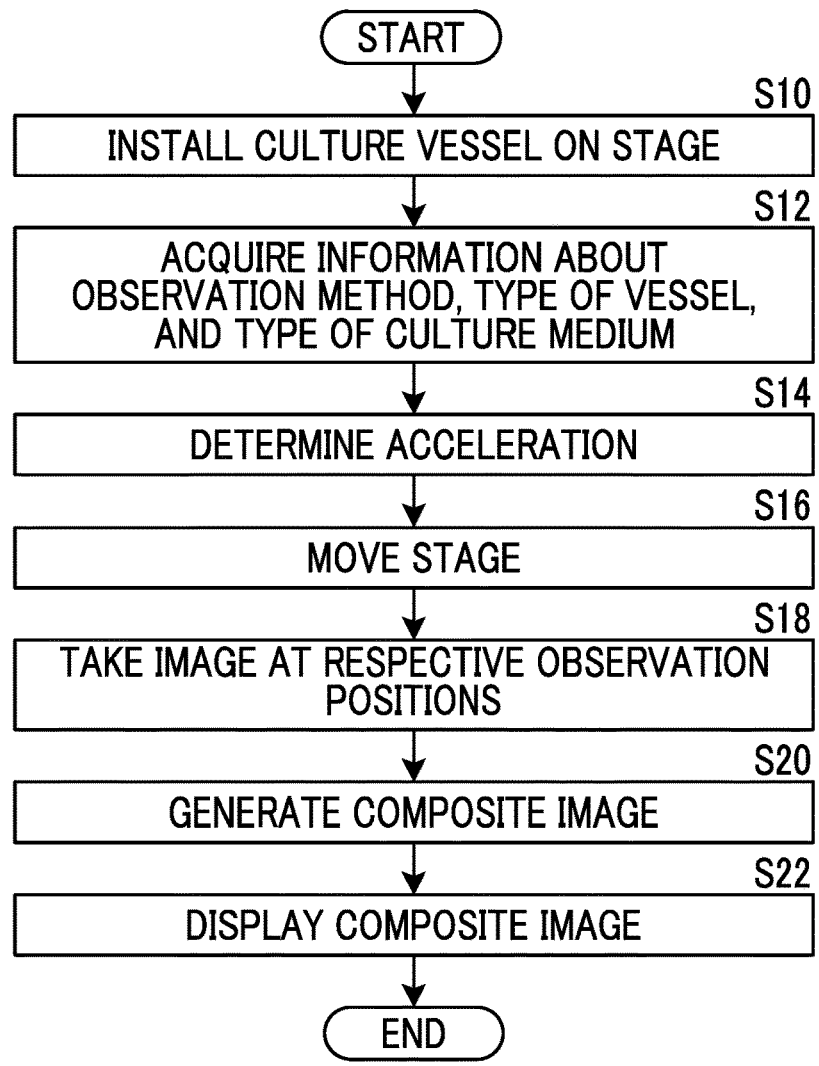
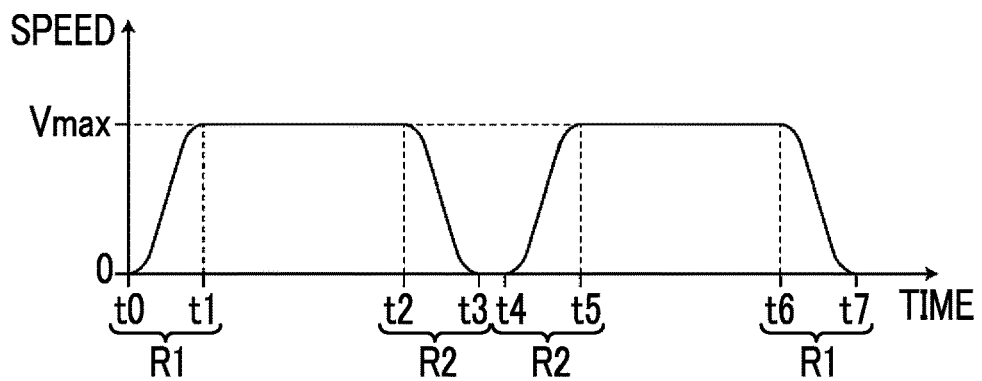

OBSERVATION DEVICE, OBSERVATION CONTROL METHOD, AND OBSERVATION CONTROL PROGRAM THAT CONTROL ACCELERATION OF A MOVEABLE STAGE HAVING AN INSTALLED SUBJECT VESSEL

CROSS-REFERENCE TO RELATED APPLICATIONS

This application is a Continuation of PCT International Application No. PCT/JP2018/005098 filed on Feb. 14, 2018, which claims priority under 35 U.S.C. § 119(a) to Japanese Patent Application No. 2017-066765 filed on Mar. 30, 2017. Each of the above application(s) is hereby expressly incorporated by reference, in its entirety, into the present application.

BACKGROUND OF THE INVENTION

1. Field of the Invention

The present invention relates to an observation device, an observation control method, and an observation control program that move a stage, on which a vessel in which a subject is stored is installed, with respect to an image-forming optical system to observe the image of the entire subject.

2. Description of the Related Art

A method including imaging pluripotent stem cells, such as an embryonic stem (ES) cell and an induced pluripotent stem (iPS) cell, differentiated and induced cells, or the like by a microscope or the like, and capturing the characteristics of the taken images to determine the differentiated state of the cells has been proposed in the past.

Pluripotent stem cells, such as an ES cell and an iPS cell, are cells that have a capability to be differentiated into cells of various tissues, and have been in the spotlight as cells that can be applied to regenerative medicine, the development of drugs, the identification of diseases, and the like.

A method, which performs so-called tilting imaging to acquire images having a high magnification and a wide field of view in a case where cells are imaged by a microscope as described above, is proposed. Specifically, for example, a method including moving a stage, on which a culture vessel, such as a well plate or a flask, is installed, with respect to an image-forming optical system to scan the respective observation positions in the culture vessel, taking images at the respective observation positions, and combining the images at the respective observation positions is proposed.

SUMMARY OF THE INVENTION

However, in a case where the respective observation positions are scanned while the stage is moved as described above, defects are generated in the images of the cells due to the fluctuation of the fluid level of a culture fluid stored in the culture vessel.

Accordingly, a method of slowly moving the stage while gradually accelerating the stage is considered. However, since long time is required until the end of the scan of all the observation positions in a case where an acceleration is set to be uniformly low in this way, imaging time is lengthened. That is, it is very difficult to make the high speed of acquisition of an image and high quality be compatible with each other.

WO2007/001002A discloses a method of controlling the transport speed of a vessel according to the type of the vessel in consideration of stress to be applied to cells, but the high speed of acquisition of an image and high quality are not compatible with each other in this method.

Further, JP2010-161950A discloses a method of changing an acceleration according to the depth of liquid to suppress vibration near the bottom of a vessel. However, JP2010-161950A also does not propose a method of making the high speed of acquisition of an image and high quality be compatible with each other.

The invention has been made in consideration with the above-mentioned problem, and an object of the invention is to provide an observation device, an observation control method, and an observation control program that make high speed of acquisition of an image and high quality be compatible with each other.

An observation device according to an aspect of the invention comprises: a stage on which a vessel in which a subject is stored is installed; an image-forming optical system that includes an objective lens forming an image of the subject stored in the vessel; a scan control unit that moves the stage with respect to the image-forming optical system to scan respective observation positions in the vessel by the image-forming optical system; and an acceleration-determination-information acquisition unit that acquires at least one piece of information among information about the subject, information about the vessel, information about an observation method, or information about an observation condition. The scan control unit controls an acceleration of the stage on the basis of the at least one piece of information.

Further, in the observation device according to the aspect of the invention, it is preferable that the information about the subject includes at least one of information about a type of a culture medium or information about an amount of the culture medium.

Furthermore, in the observation device according to the aspect of the invention, the information about the vessel may be information representing any one of a well plate, a flask, or a slide glass.

Further, in the observation device according to the aspect of the invention, the information about the vessel can be information representing the well plate and the scan control unit may set the acceleration to be higher as the number of wells of the well plate is larger.

Furthermore, in the observation device according to the aspect of the invention, the information about the observation method may be information representing any one of phase-difference observation, fluorescence observation, bright-field observation, differential interference observation, epi-illumination observation, or transmission observation.

Further, in the observation device according to the aspect of the invention, the scan control unit may set an acceleration in a case of the phase-difference observation to be lower than an acceleration in a case of the bright-field observation.

Furthermore, in the observation device according to the aspect of the invention, the scan control unit may set an acceleration in a case of the bright-field observation to be lower than an acceleration in a case of the epi-illumination observation.

Further, in the observation device according to the aspect of the invention, it is preferable that the information about the observation condition includes at least one of information about magnification of the objective lens, information about exposure time of an imaging element taking an image formed by the image-forming optical system, information about brightness of light emitted from a light source, or information about a wavelength of the light.

Furthermore, in the observation device according to the aspect of the invention, the information about the observation condition can be information about magnification of the objective lens and the scan control unit may set the acceleration to be lower as the magnification of the objective lens is higher.

Further, in the observation device according to the aspect of the invention, the scan control unit may make the stage reciprocate and may control an acceleration in a forward movement start period and an acceleration in a backward movement start period.

An observation control method according to another aspect of the invention is an observation control method of moving a stage, on which a vessel in which a subject is stored is installed, with respect to an image-forming optical system, which includes an objective lens forming an image of the subject stored in the vessel, to scan respective observation positions in the vessel by the image-forming optical system. The observation control method comprises: acquiring at least one piece of information among information about the subject, information about the vessel, information about an observation method, or information about an observation condition; and controlling an acceleration of the stage on the basis of the acquired at least one piece of information.

An observation control program according to still another aspect of the invention is an observation control program causing a computer to perform a procedure for moving a stage, on which a vessel in which a subject is stored is installed, with respect to an image-forming optical system, which includes an objective lens forming an image of the subject stored in the vessel, to scan respective observation positions in the vessel by the image-forming optical system. The observation control program causes the computer to perform a procedure for acquiring at least one piece of information among information about the subject, information about the vessel, information about an observation method, or information about an observation condition, and a procedure for controlling an acceleration of the stage on the basis of the acquired at least one piece of information.

According to the observation device, the observation control method, and the observation control program of the aspects of the invention, in a case where a stage on which the vessel in which the subject is stored is installed is moved with respect to the image-forming optical system, so that the respective observation positions in the vessel are scanned by the image-forming optical system, at least one piece of information is acquired among information about the subject, information about the vessel, information about an observation method, or information about an observation condition, and an acceleration of the stage is controlled on the basis of the acquired at least one piece of information. Accordingly, a good image can be acquired quickly.

BRIEF DESCRIPTION OF THE DRAWINGS

FIGS. 4A, 4B, and 4C are diagrams showing examples of acceleration tables.

FIG. 5 is a flowchart illustrating the action of the microscopic observation system that uses the observation device according to the embodiment of the invention.

FIG. 6 is a diagram showing another example of a change in the speed of the stage.

DESCRIPTION OF THE PREFERRED EMBODIMENTS

Figure 1:
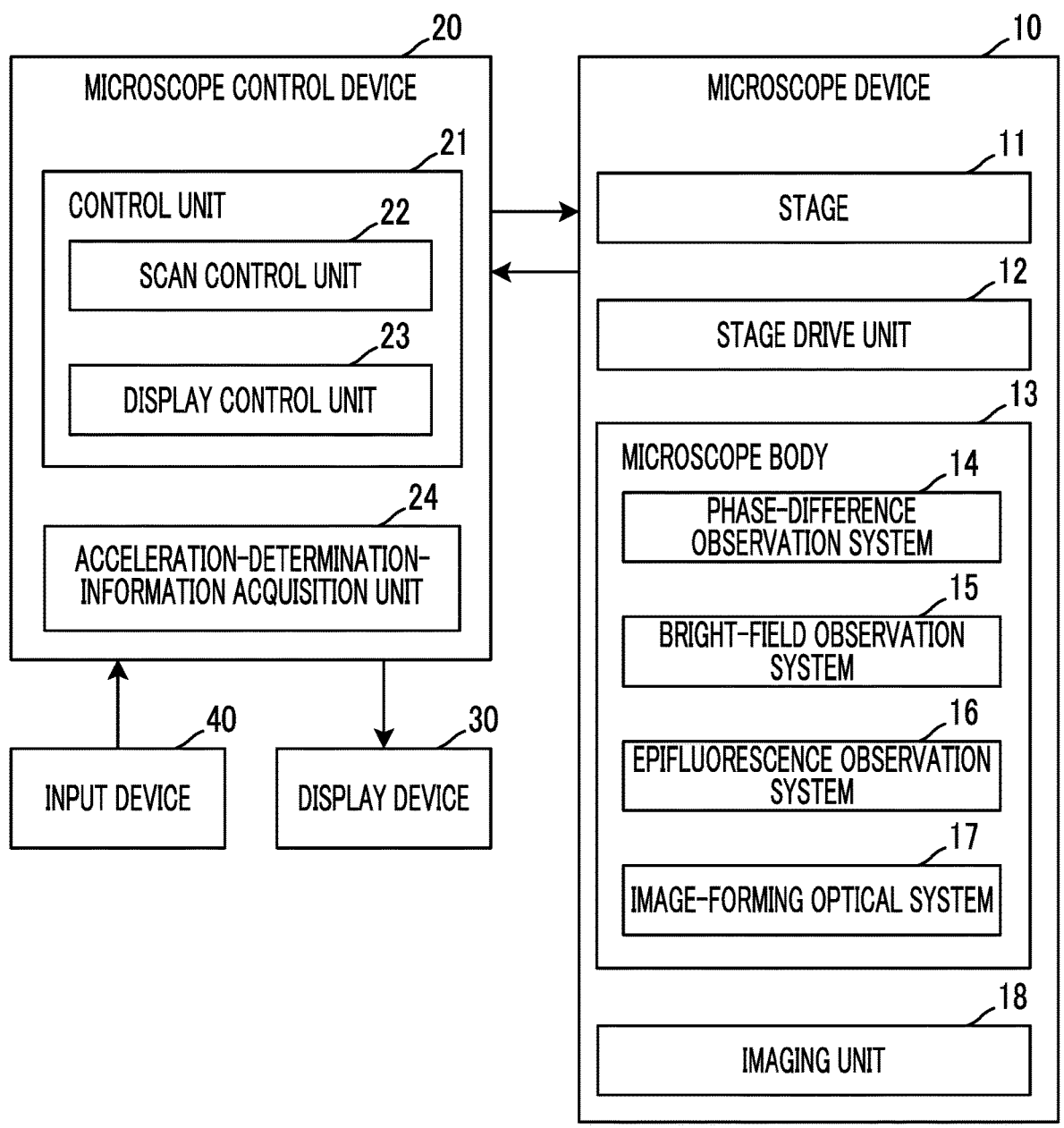
FIG. 1 is a block diagram showing the schematic configuration of a microscopic observation system that uses an observation device according to an embodiment of the invention.

A microscopic observation system that uses an observation device, an observation control method, and an observation control program according to an embodiment of the invention will be described in detail below with reference to the drawings. FIG. 1 is a block diagram showing the schematic configuration of a microscopic observation system of this embodiment.

As shown in FIG. 1, the microscopic observation system of this embodiment comprises a microscope device 10, a microscope control device 20, a display device 30, and an input device 40. In this embodiment, a stage 11 and an image-forming optical system 17 of the microscope device 10 and a scan control unit 22 and an acceleration-determination-information acquisition unit 24 of the microscope control device 20 correspond to an observation device of the invention.

The microscope device 10 comprises a stage 11, a stage drive unit 12, a microscope body 13, and an imaging unit 18.

A culture vessel (corresponding to a vessel of the invention) in which a subject is stored is installed on the stage 11, and the stage 11 is moved by the stage drive unit 12.

There are a well plate including a plurality of wells, a flask, a slide glass, and the like as the culture vessel to be installed on the stage 11. Further, examples of cells stored in the culture vessel include: pluripotent stem cells, such as an iPS cell and an ES cell; the cells of the nerve, the skin, the cardiac muscle, and the liver that are differentiated and induced from stem cells; the cells of the skin, the retina, the cardiac muscle, the blood cells, the nerve, and the organ obtained from the human body; and the like. Furthermore, a culture medium, such as culture fluid, is stored in the culture vessel together with these cells. In this specification, an object to be observed, such as the above-mentioned cells, and the culture medium are referred to as the subject together.

The stage drive unit 12 comprises an actuator that includes a piezoelectric element and the like, and moves the stage 11 according to a control signal that is output from the scan control unit 22 of the microscope control device 20. Specifically, the stage drive unit 12 moves the stage 11 in an X direction and a Y direction that are orthogonal to each other in a horizontal plane. The stage 11 on which the culture vessel is installed is moved with respect to the image-forming optical system 17 of the microscope device 10 in this way, so that the respective observation positions in the culture vessel are scanned by the image-forming optical system 17.

The microscope body 13 comprises the image-forming optical system 17 that includes an objective lens forming the image of the subject stored in the culture vessel, a light source that irradiates the subject with light, and the like. The microscope body 13 of this embodiment is adapted to allow a user to observe the subject stored in the culture vessel by a plurality of observation methods. Specifically, the microscope body 13 comprises a phase-difference observation system 14, a bright-field observation system 15, and an epifluorescence observation system 16.

The phase-difference observation system 14 forms the phase-difference image of the subject, and includes a white light source, a condenser lens, a slit plate in which a ring-shaped slit is formed, an objective lens, a phase plate, and the like. In the phase-difference observation system 14, white light emitted from the white light source is applied to the subject through the condenser lens and the slit plate, transmitted light transmitted through the subject is incident on the objective lens and the phase plate, and the phase-difference image caused by the interference between diffracted light and direct light emitted from the phase plate is formed.

The bright-field observation system 15 forms the bright-field image of the subject, and includes a white light source, a condenser lens, an objective lens, and the like. The bright-field observation system 15 of this embodiment performs transmission observation, so that white light emitted from the white light source is applied to the subject through the condenser lens and transmitted light transmitted through the subject is incident on the objective lens, and the bright-field image is formed.

The epifluorescence observation system 16 forms a fluorescence image that is emitted from the subject by the irradiation of the subject with excitation light, and includes an excitation light source, an excitation filter, a dichroic mirror, an objective lens, and the like. The epifluorescence observation system 16 of this embodiment performs epi-illumination observation, so that excitation light emitted from the excitation light source is transmitted through the excitation filter, is reflected by the dichroic mirror, is transmitted through the objective lens, and is then applied to the subject from the bottom side of the culture vessel. Further, the epifluorescence observation system 16 is adapted so that fluorescence, which is emitted from cells and the like toward the bottom of the culture vessel, is incident on the objective lens again and forms a fluorescence image and the fluorescence image is transmitted through the dichroic mirror. Since fluorescence emitted from the cells and the like is not transmitted through the culture fluid stored in the culture vessel as described above in the epifluorescence observation system 16, there is little influence of the fluctuation of the fluid level of the culture fluid that is caused by the movement of the stage 11.

The image-forming optical system 17 shown in FIG. 1 means all the respective image-forming optical systems of the phase-difference observation system 14, the bright-field observation system 15, and the epifluorescence observation system 16 having been described above; and a part or all of the respective image-forming optical systems of the respective observation systems may be in common with each other or the respective image-forming optical systems of the respective observation systems may be formed separately.

Further, the image-forming optical system 17 (the image-forming optical system of each observation system) is adapted to be movable in the direction of the optical axis of the objective lens, so that auto-focus control is performed and the contrast of an image to be taken by an imaging element of the imaging unit 18 is adjusted.

The imaging unit 18 comprises an imaging element that takes the phase-difference image, the bright-field image, and the fluorescence image formed by the image-forming optical system 17. A charge-coupled device (CCD) image sensor, a complementary metal-oxide semiconductor (CMOS) image sensor, or the like is used as the imaging element. An imaging element, which is provided with red, green, and blue (RGB) color filters, may be used as the imaging element, and a monochroic imaging element may be used as the imaging element. Further, the imaging element may be separately provided for every observation system, and may be shared by a plurality of observation systems. An image signal output from the imaging element of the imaging unit 18 is input to the microscope control device 20.

Next, the configuration of the microscope control device 20 will be described. The microscope control device 20 controls the entire microscope device 10, and comprises a control unit 21 and an acceleration-determination-information acquisition unit 24. Further, the control unit 21 comprises a scan control unit 22 and a display control unit 23.

The microscope control device 20 is formed of a computer that comprises a central processing unit, a semiconductor memory, a hard disk drive, and the like; and an observation control program according to an embodiment of the invention is installed on the hard disk drive. Furthermore, the observation control program is executed by a central processing unit included in the control unit 21, so that the scan control unit 22, the display control unit 23, and the acceleration-determination-information acquisition unit 24 shown in FIG. 1 function. In this embodiment, the functions of the scan control unit 22, the display control unit 23, and the acceleration-determination-information acquisition unit 24 are realized by the execution of the observation control program. However, the invention is not limited to the configuration where the functions are realized by only the processing of the program, and some functions may be realized by hardware, such as an integrated circuit (IC). The observation control program may be stored in a non-transitory computer-readable recording medium and may be read by the computer that forms the microscope control device 20. Further, the observation control program may be transmitted through a network.

The scan control unit 22 drives and controls the stage drive unit 12, so that the stage 11 is moved in the X direction and the Y direction.

The display control unit 23 combines images at the respective observation positions, which are taken by the microscope device 10, to generate one composite image, and makes the display device 30 display the composite image.

The acceleration-determination-information acquisition unit 24 acquires information about the observation method, information about the type of the vessel, and information about the subject that are set and input by a user using the input device 40.

The information about the observation method means information representing which observation system is to be used among the observation systems of the microscope body 13. Specifically, the information about the observation method is information representing any one of phase-difference observation, fluorescence observation, bright-field observation, differential interference observation, epi-illumination observation, or transmission observation.

The information about the type of the vessel means information representing the type of the vessel storing cells and the like that are an object to be observed. Specifically, the information about the type of the vessel is information representing any one of a well plate, a flask, or a slide glass. The information about the type of the vessel corresponds to information about a vessel of the invention.

The information about the subject means information about the culture medium that is the subject. The information about the subject includes at least one of information about the type of the culture medium or information about the amount of the culture medium.

The display device 30 displays the composite image that is generated by the display control unit 23 as described above, and includes, for example, a liquid crystal display.

The input device 40 comprises a mouse, a keyboard, and the like and receives the inputs of various kinds of setting that are performed by a user. The input device 40 of this embodiment receives the inputs of setting of the information about the observation method, the information about the type of the vessel, and the information about the subject that have been described above. Further, the input device 40 is formed of a touch panel, and may be used as the display device 30.

In this embodiment, the stage 11 is moved in the X direction Y and the direction by control, which is performed by the scan control unit 22, as described above, so that the respective observation positions in the culture vessel are two-dimensionally scanned and images at the respective observation positions are taken.

Figure 2:
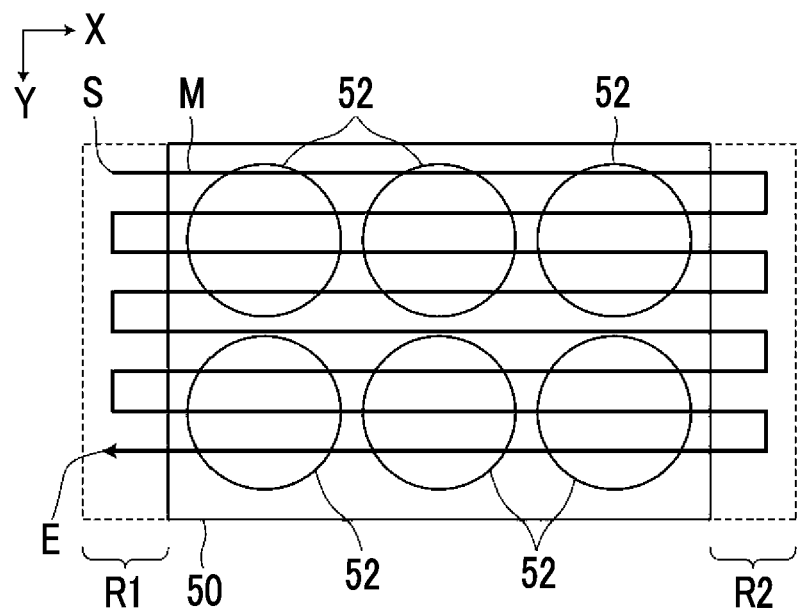
FIG. 2 is a diagram showing an example of a scanning trajectory of each observation position in a well plate.

FIG. 2 is a diagram showing a scanning trajectory of each observation position by a solid line M in a case where a well plate 50 including six wells 52 is used as the culture vessel. As shown in FIG. 2, the respective observation positions in the well plate 50 are scanned along the solid line M to a scan end point E from a scan start point S through the movement of the stage 11 in the X direction and the Y direction. That is, after being scanned in a positive direction of the X direction (rightward in FIG. 2), the observation positions are scanned in a positive direction of the Y direction (downward in FIG. 2) and are scanned in a negative direction of the X direction (leftward in FIG. 2). Then, the observation positions are scanned in the positive direction of the Y direction again, and are scanned in the positive direction of the X direction again. The reciprocating movement of the stage 11 in the X direction and the movement of the stage 11 in the Y direction are repeatedly performed in this way, so that the observation positions are two-dimensionally scanned in the well plate 50.

Figure 3:
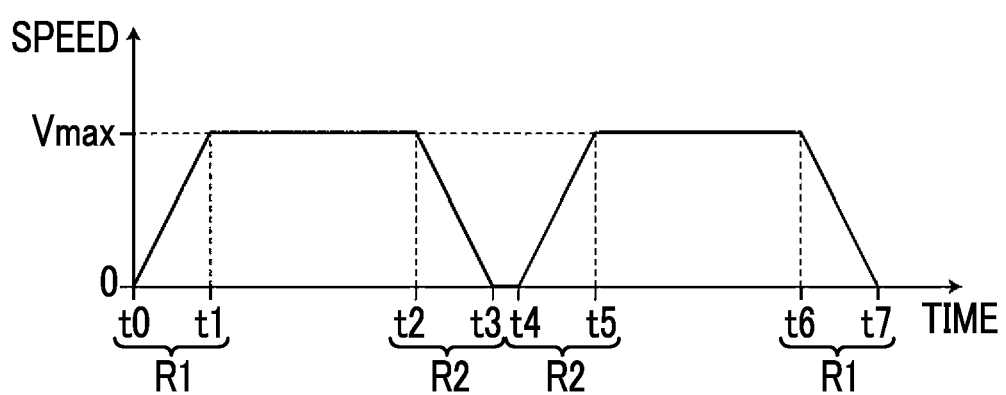
FIG. 3 is a diagram showing an example of a change in the speed of a stage.

Further, the scan control unit 22 of this embodiment makes the stage 11 move with a preset acceleration in the forward movement start period and the backward movement start period of the stage 11 to scan the respective observation positions in the well plate 50 at a constant speed. FIG. 3 is a diagram showing an example of a change in the speed of the stage 11. In a case where the stage 11 is moved forward, as shown in FIG. 3, the scan control unit 22 accelerates the stage 11 with a constant acceleration in a forward movement start period (t0 to t1), that is, a period where a region R1 shown in FIG. 2 (an outer end portion of the well plate 50 not including the observation positions in the well plate 50) is scanned and decelerates the stage 11 with a constant acceleration in a forward movement end period (t2 to t3), that is, a period where a region R2 shown in FIG. 2 (an outer end portion of the well plate 50 not including the observation positions in the well plate 50) is scanned. Further, in a case where the stage 11 is moved backward, the scan control unit 22 accelerates the stage 11 with a constant acceleration in a backward movement start period (t4 to t5), that is, a period where a region R2 shown in FIG. 2 is scanned and decelerates the stage 11 with a constant acceleration in a backward movement end period (t6 to t7), that is, a period where a region R1 shown in FIG. 2 is scanned.

Further, the scan control unit 22 changes accelerations in the forward movement start period, the forward movement end period, the backward movement start period, and the backward movement end period according to the observation method, the type of the culture vessel, and the type of the culture medium. Specifically, acceleration tables for the respective observation methods shown in FIGS. 4A to 4C are set in the scan control unit 22 in advance. Furthermore, the scan control unit 22 changes an acceleration according to which observation system is to be used among the phase-difference observation system 14, the bright-field observation system 15, and the epifluorescence observation system 16, the type of the culture vessel, and the type of the culture medium. The maximum speed V max shown in FIG. 3 may be set in advance, or may be set and input by a user using the input device 40.

In this embodiment, information about well plates including 6 wells, 12 wells, 48 wells, and 96 wells is set as the information about the type of the culture vessel and information about a culture medium B1, a culture medium B2, and a culture medium B3 is set as the information about the type of the culture medium. Since the respective well plates have the same size, the volumes (opening areas) of wells are smaller as the number of the wells is larger. Further, the viscosities of the culture mediums B1, B2, and B3 are different from each other, the viscosity of the culture medium B1 is lowest, the viscosity of the culture medium B3 is highest, and the viscosity of the culture medium B2 is set to a viscosity between the viscosity of the culture medium B1 and the viscosity of the culture medium B3.

In regard to the magnitudes of accelerations A1 to A36, first, in a case where the conditions of the type of the vessel and the type of the culture medium are the same, among a phase-difference observation method, a bright-field observation method, and an epifluorescence observation method, an acceleration in the case of a phase-difference observation method is set to be lowest, an acceleration in the case of an epifluorescence observation method is set to be highest, and an acceleration in the case of a bright-field observation method is set to an acceleration between the acceleration in the case of the phase-difference observation method and the acceleration in the case of the epifluorescence observation method. Specifically, for example, in a case where the type of the vessel corresponds to a well plate including 6 wells and the type of the culture medium is the same as that of the culture medium B1, an acceleration in the case of the phase-difference observation method is denoted by A1, an acceleration in the case of the bright-field observation method is denoted by A13, and an acceleration in the case of the epifluorescence observation method is denoted by A25. Further, a relationship between the accelerations in the cases of the respective observation methods satisfies "A1<A13<A25". Since a phase-difference image, which is formed by the phase-difference observation method, is likely to be affected by the fluctuation of a fluid level that is caused by the movement of the stage 11, it is preferable that an acceleration is low. On the other hand, since it is most difficult for a fluorescence image, which is formed by the epifluorescence observation method, to be affected by the fluctuation of a fluid level that is caused by the movement of the stage 11 as described above, it is preferable that an acceleration is high. An acceleration is changed in this way by each observation method, so that an image can be more quickly acquired.

Next, in regard to an acceleration corresponding to the type of the vessel, in a case where the conditions of an observation method and the type of the culture medium are the same, an acceleration is set to be higher as the number of wells is larger. The reason for this is that it is difficult for an image to be affected by the fluctuation of a fluid level that is caused by the movement of the stage 11 since the volumes (opening areas) of wells are smaller as the number of the wells is larger. Specifically, for example, in a case where the observation method is a phase-difference observation method and the type of the culture medium is the same as the type of the culture medium B1, an acceleration in the case of a well plate including 6 wells is denoted by A1, an acceleration in the case of a well plate including 12 wells is denoted by A4, an acceleration in the case of a well plate including 48 wells is denoted by A7, and an acceleration in the case of a well plate including 96 wells is denoted by A10. Further, a relationship between the accelerations in the cases of the respective numbers of wells satisfies "A1<A4<A7<A10".

Next, in regard to an acceleration corresponding to the type of the culture medium, in a case where the conditions of an observation method and the type of the vessel are the same, an acceleration is set to be higher as the viscosity of the culture medium is higher. The reason for this is that it is difficult for an image to be affected by the fluctuation of a fluid level that is caused by the movement of the stage 11 as the viscosity of the culture medium is higher. Specifically, for example, in a case where the observation method is a phase-difference observation method and the type of the vessel is the same as the type of a well plate including 6 wells, an acceleration in the case of a culture medium B1 is denoted by A1, an acceleration in the case of a culture medium B2 is denoted by A2, and an acceleration in the case of a culture medium B3 is denoted by A3. Further, a relationship between the accelerations in the cases of the respective culture mediums satisfies "A1<A2<A3".

The scan control unit 22 determines an acceleration with reference to the tables of FIGS. 4A to 4C on the basis of the information about the observation method, the information about the type of the vessel, and the information about the type of the culture medium, which are set and input by a user, and controls the acceleration of the stage 11 in the forward movement start period, the forward movement end period, the backward movement start period, and the backward movement end period.

Next, the action of the microscopic observation system of this embodiment will be described with reference to a flowchart shown in FIG. 5.

First, a culture vessel in which a subject is stored is installed on the stage 11 (S10). Then, the information about the observation method, the information about the type of the vessel, and the information about the type of the culture medium are set and input by a user using the input device 40, are acquired by the acceleration-determination-information acquisition unit 24, and are output to the scan control unit 22 (S12). The scan control unit 22 determines the acceleration of the stage 11 in the forward movement start period, the forward movement end period, the backward movement start period, and the backward movement end period with reference to the tables shown in FIGS. 4A to 4C on the basis of the input information (S14).

Then, the stage drive unit 12 is driven and controlled on the basis of the acceleration, which is determined in S14, by the scan control unit 22, so that the stage 11 reciprocates (S16).

After that, the respective observation positions in the culture vessel are scanned through the movement of the stage 11, the images of cells and the like are formed by an observation system corresponding to the observation method that is set and input by a user, and the images at the respective observation positions are taken by the imaging unit 18 (S18).

The images at the respective observation positions, which are taken by the imaging unit 18, are output to the display control unit 23, and the display control unit 23 combines the images at the respective observation positions to generate a composite image (S20), and makes the display device 30 display the generated composite image (S22).

According to the microscopic observation system of the embodiment, since the acceleration of the stage 11 is changed according to the observation method, the type of the culture vessel, and the type of the culture medium, the influence of the fluid level of culture fluid caused by the movement of the stage 11 can be suppressed. Further, since the stage 11 may be moved at as high speed as possible, a good image can be acquired as quickly as possible.

The acceleration of the stage 11 is changed according to the observation method, the type of the culture vessel, and the type of the culture medium in the embodiment, but the acceleration-determination-information acquisition unit 24 may acquire information about the amount of the culture medium and the scan control unit 22 may control the acceleration of the stage 11 according to the information about the amount of the culture medium. Specifically, since the influence of the fluctuation of a fluid level on the image to be formed is larger as the amount of the culture medium is larger, the acceleration of the stage 11 may be set to be lower as the amount of the culture medium is larger. The information about the amount of the culture medium may be set and input by a user using the input device 40, or a weight sensor or the like may be provided to automatically measure the amount of the culture medium.

Further, in the embodiment, the acceleration-determination-information acquisition unit 24 may acquire information about an observation condition, and the scan control unit 22 may control the acceleration of the stage 11 according to the information about the observation condition. For example, there is information about the magnification of the objective lens of the image-forming optical system 17 as the information about the observation condition. Specifically, since the influence of the fluctuation of a fluid level on the image to be formed is larger as the magnification of the objective lens is higher, the acceleration of the stage 11 may be set to be lower as the magnification of the objective lens is higher. The information about the magnification of the objective lens may be set and input by a user using the input device 40, or may be automatically acquired from information, such as a bar code given to the objective lens.

Furthermore, the acceleration-determination-information acquisition unit 24 may acquire information about the exposure time of the imaging element of the imaging unit 18 as the information about the observation condition, and the scan control unit 22 may control the acceleration of the stage 11 according to the information about the exposure time. Specifically, since the influence of the fluctuation of a fluid level on an image to be taken by the imaging element is larger as the exposure time of the imaging element is shorter, the acceleration of the stage 11 may be set to be lower as the exposure time is shorter. The information about the exposure time may be set and input by a user using the input device 40, or may be automatically acquired from information that is separately set and input as the control information about the imaging element.

Further, the acceleration-determination-information acquisition unit 24 may acquire information about the brightness or wavelength of light, which is emitted from the light source of the observation system, as the information about the observation condition and the scan control unit 22 may control the acceleration of the stage 11 according to the information about the brightness or wavelength of the light. Specifically, since the influence of the fluctuation of a fluid level is larger as the brightness of the light emitted from the light source of the observation system is higher, the acceleration of the stage 11 may be set to be lower as the brightness is higher. The information about the brightness may be set and input by a user using the input device 40, or may be automatically detected using an optical sensor or the like. Furthermore, since the influence of the fluctuation of a fluid level is larger as the wavelength of light emitted from the light source of the observation system is shorter, the acceleration of the stage 11 may be set to be lower as the wavelength is shorter. The information about the wavelength of the light may be set and input by a user using the input device 40.

Further, the information about well plates of which the numbers of wells are different from each other has been acquired as the information about the type of the culture vessel in the embodiment. However, in a case where a flask or a slide glass is used as the culture vessel, the information about the culture vessel of these vessels may be acquired and the acceleration of the stage 11 may be controlled according to the type of the culture vessel. Specifically, since the storage volume of the flask is larger than that of each well of a well plate, the fluctuation of a fluid level in the flask is also large. Accordingly, acceleration in a case where a flask is used may be set to be lower than that in a case where a well plate is used as the culture vessel. Furthermore, there is little influence of the fluctuation of a fluid level in a case where a slide glass is used as the culture vessel. Accordingly, acceleration in a case where a slide glass is used may be set to be larger than that in a case where a well plate is used as the culture vessel.

Further, the phase-difference observation system 14, the bright-field observation system 15, and the epifluorescence observation system 16 have been provided as the observation systems in the embodiment, but a differential interference observation system may be provided in addition to these observation systems or instead of these observation systems. In a case where the differential interference observation system is formed of a transmission observation system as in the phase-difference observation system 14, the influence of the fluctuation of a fluid level on a differential interference image in the phase-difference observation system is larger than that in the bright-field observation system 15. Accordingly, acceleration in a case where the differential interference observation system is used may be set to be lower than that in a case where the bright-field observation system 15 is used. In regard to a relationship between acceleration in a case where the phase-difference observation system 14 is used and acceleration in a case where the differential interference observation system is used, it is preferable that the acceleration in a case where the differential interference observation system is used is set to be lower than the acceleration in a case where the phase-difference observation system 14 is used.

Furthermore, the microscopic observation system may be adapted to warn a user to urge the user to set acceleration again, to take an image again, and the like in a case where the fluctuation of a fluid level affects a taken image even though the acceleration of the stage 11 is controlled as in the embodiment. Specifically, the microscopic observation system may be adapted to analyze a taken image to extract contrast failure and to warn a user in a case where the contrast failure is equal to or higher than a preset threshold value. This contrast failure is caused in a case where the shading of the entire image deteriorates due to the influence of the fluctuation of a fluid level and low-frequency contrast fluctuates. Further, the contrast failure is caused in a case where a low-contrast phase-difference image is taken due to the influence of the fluctuation of a fluid level.

Further, the stage 11 has been accelerated and decelerated with a constant acceleration as shown in FIG. 3 in the embodiment, but the invention is not limited thereto. The stage 11 may be accelerated and decelerated while an acceleration is changed as shown in FIG. 6.

Furthermore, an acceleration has been determined from three conditions of the observation method, the type of the culture vessel, and the type of the culture medium in the embodiment, but may be determined on the basis of one condition among them. Further, a user can select a condition to be used in a case where an acceleration is to be determined. The same applies to the amount of the culture medium and the observation condition.

EXPLANATION OF REFERENCES

10: microscope device
11: stage
12: stage drive unit
13: microscope body
14: phase-difference observation system
15: bright-field observation system
16: epifluorescence observation system
17: image-forming optical system
18: imaging unit
20: microscope control device
21: control unit
22: scan control unit
23: display control unit
24: acceleration-determination-information acquisition unit
30: display device
40: input device
50: well plate
52: well
E: scan end point
M: solid line showing scanning trajectory
S: scan start point

What is claimed is:
1. An observation device comprising:
a stage on which a vessel in which a subject is stored is installed;
an image-forming optical system that includes an objective lens forming an image of the subject stored in the vessel;
a scan control unit that moves the stage with respect to the image-forming optical system to scan respective observation positions in the vessel by the image-forming optical system; and
an acceleration-determination-information acquisition unit that acquires at least one piece of information among information about the subject, information about the vessel, information about an observation method, or information about an observation condition,
wherein the scan control unit controls an acceleration of the stage based on the at least one piece of information, and
wherein the information about the observation method is information representing any one of phase-difference observation, fluorescence observation, bright-field observation, differential interference observation, epi-illumination observation, or transmission observation.

2. The observation device according to claim 1,
wherein the information about the subject includes at least one of information about a type of a culture medium or information about an amount of the culture medium.

3. The observation device according to claim 1,
wherein the information about the vessel is information representing any one of a well plate, a flask, or a slide glass.

4. The observation device according to claim 2,
wherein the information about the vessel is information representing any one of a well plate, a flask, or a slide glass.

5. The observation device according to claim 3,
wherein the information about the vessel is information representing the well plate, and
the scan control unit sets the acceleration to be higher as the number of wells of the well plate is larger.

6. The observation device according to claim 4,
wherein the information about the vessel is information representing the well plate, and
the scan control unit sets the acceleration to be higher as the number of wells of the well plate is larger.

7. The observation device according to claim 2,
wherein the information about the observation method is information representing any one of phase-difference observation, fluorescence observation, bright-field observation, differential interference observation, epi-illumination observation, or transmission observation.

8. The observation device according to claim 3,
wherein the information about the observation method is information representing any one of phase-difference observation, fluorescence observation, bright-field observation, differential interference observation, epi-illumination observation, or transmission observation.

9. The observation device according to claim 4,
wherein the information about the observation method is information representing any one of phase-difference observation, fluorescence observation, bright-field observation, differential interference observation, epi-illumination observation, or transmission observation.

10. The observation device according to claim 5,
wherein the information about the observation method is information representing any one of phase-difference observation, fluorescence observation, bright-field observation, differential interference observation, epi-illumination observation, or transmission observation.

11. The observation device according to claim 6,
wherein the information about the observation method is information representing any one of phase-difference observation, fluorescence observation, bright-field observation, differential interference observation, epi-illumination observation, or transmission observation.

12. The observation device according to claim 7,
wherein the scan control unit sets an acceleration in a case of the phase-difference observation to be lower than an acceleration in a case of the bright-field observation.

13. The observation device according to claim 1,
wherein the information about the observation condition includes at least one of information about magnification of the objective lens, information about exposure time of an imaging element taking an image formed by the image-forming optical system, information about brightness of light emitted from a light source, or information about a wavelength of the light.

14. The observation device according to claim 13,
wherein the information about the observation condition is information about magnification of the objective lens, and
the scan control unit sets the acceleration to be lower as the magnification of the objective lens is higher.

15. The observation device according to claim 1,
wherein the scan control unit makes the stage reciprocate and controls an acceleration in a forward movement start period and an acceleration in a backward movement start period.

16. An observation control method of the observation device according to claim 1, which performs a procedure for moving the stage, on which the vessel in which the subject is stored is installed, with respect to the image-forming optical system, which includes the objective lens forming the image of the subject stored in the vessel, to scan respective observation positions in the vessel by the image-forming optical system, the observation control method comprising:
acquiring at least one piece of information among the information about the subject, the information about the vessel, the information about the observation method, or the information about the observation condition; and
controlling the acceleration of the stage on the basis of the acquired at least one piece of information.

17. A non-transitory computer readable recording medium storing an observation control program causing a computer to perform as the observation device according to claim 1, by performing a procedure for moving the stage, on which the vessel in which the subject is stored is installed, with respect to the image-forming optical system, which includes the objective lens forming the image of the subject stored in the vessel, to scan respective observation positions in the vessel by the image-forming optical system, the observation control program causing the computer to perform
a procedure for acquiring at least one piece of information among the information about the subject, the information about the vessel, the information about the observation method, or the information about the observation condition; and
a procedure for controlling the acceleration of the stage on the basis of the acquired at least one piece of information.

* * * * *